US007338536B2

(12) United States Patent
Sabelle et al.

(10) Patent No.: US 7,338,536 B2
(45) Date of Patent: Mar. 4, 2008

(54) N-ALKYLAMINO SECONDARY PARA-PHENYLENEDIAMINE, COMPOSITION FOR DYEING KERATIN FIBERS COMPRISING SUCH A PARA-PHENYLENEDIAMINE, PROCESSES USING THIS COMPOSITION AND USES THEREOF

(75) Inventors: Stéphane Sabelle, Paris (FR); Alain Genet, Aulnay Sous Bois (FR)

(73) Assignee: L'Oreal S. A., Paris (FR)

( * ) Notice: Subject to any disclaimer, the term of this patent is extended or adjusted under 35 U.S.C. 154(b) by 182 days.

(21) Appl. No.: 11/066,456

(22) Filed: Feb. 28, 2005

(65) Prior Publication Data

US 2006/0026772 A1    Feb. 9, 2006

Related U.S. Application Data

(60) Provisional application No. 60/569,645, filed on May 11, 2004.

(30) Foreign Application Priority Data

Feb. 27, 2004    (FR)    ................... 04 02022

(51) Int. Cl.
*A61K 7/13* (2006.01)
(52) U.S. Cl. .................. 8/405; 8/406; 8/408; 8/409; 8/410; 8/412; 8/415; 8/421; 546/184; 548/400
(58) Field of Classification Search .............. 8/405, 8/406, 408, 409, 410, 412, 415, 421; 546/184; 548/400
See application file for complete search history.

(56) References Cited

U.S. PATENT DOCUMENTS

| | | | | |
|---|---|---|---|---|
| 3,658,454 | A | * | 4/1972 | Paul .............................. 8/416 |
| 4,003,699 | A | | 1/1977 | Rose et al. |
| 4,007,747 | A | | 2/1977 | Kalopissis et al. |
| RE30,199 | E | | 1/1980 | Rose et al. |
| 4,330,291 | A | | 5/1982 | Buguat et al. |
| 4,361,516 | A | | 11/1982 | Kalopissis et al. |
| 4,473,374 | A | | 9/1984 | Bugaut et al. |
| 4,823,985 | A | | 4/1989 | Grollier et al. |
| 5,061,289 | A | | 10/1991 | Clausen et al. |
| 5,380,340 | A | | 1/1995 | Neunhoeffer et al. |
| 5,534,267 | A | | 7/1996 | Neunhoeffer et al. |
| 5,663,366 | A | | 9/1997 | Neunhoeffer et al. |
| 5,708,151 | A | | 1/1998 | Möckli |
| 5,766,576 | A | | 6/1998 | Löwe et al. |
| 6,099,592 | A | | 8/2000 | Vidal et al. |
| 6,284,003 | B1 | | 9/2001 | Rose et al. |
| 6,638,965 | B2 | | 10/2003 | Walter et al. |
| 6,730,789 | B1 | | 5/2004 | Birault et al. |
| 7,160,901 | B2 | | 1/2007 | Walter et al. |
| 7,166,615 | B2 | | 1/2007 | Walter et al. |

2004/0009613 A1    1/2004    Zhou et al.

FOREIGN PATENT DOCUMENTS

| | | |
|---|---|---|
| DE | 21 35 584 | 2/1972 |
| DE | 23 59 399 | 6/1975 |
| DE | 29 34 331 A1 | 3/1981 |
| DE | 38 43 892 A1 | 6/1990 |
| DE | 41 33 957 A1 | 4/1993 |
| DE | 195 43 988 A1 | 5/1997 |
| EP | 0 714 954 B1 | 6/1996 |
| EP | 0 770 375 B1 | 2/1997 |
| FR | 2 254 557 | 7/1975 |
| FR | 2 315 256 | 1/1977 |
| FR | 2 586 913 A1 | 3/1987 |
| FR | 2 733 749 A1 | 11/1996 |
| FR | 2 801 308 A1 | 5/2001 |
| GB | 1 026 978 | 4/1966 |
| GB | 1 153 196 | 5/1969 |
| GB | 1 287 343 | 8/1972 |
| JP | 02-19576 | 1/1990 |
| JP | 05-163124 | 6/1993 |
| WO | WO 94/08969 A1 | 4/1994 |
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 01/64656 A1 | 9/2001 |
| WO | WO 02/36564 A1 | 5/2002 |
| WO | WO 03/027102 A1 | 4/2003 |

OTHER PUBLICATIONS

STIC Search Report dated Mar. 14, 2007.*
French search report for FR 04 02022 (Priority Application for U.S. Appl. No. 11/066,456), Sep. 15, 2004.
Szekeres et al. "N-(ω-Aminoalkyl)-Phthalimide Derivatives, A New Group With Antifibrillatory Action." Acta Physiol. Acad. Sci. Hung. 1965, 26(3), 287-295.
XP002295408: Catalog, ComGenex Product List, Jun. 2003. ComGenex International Inc, Monmouth, US.
English language Derwent abstract of DE 21 35 584, 1972.
English language Derwent abstract of DE 29 34 331, 1981.
English language Derwent abstract of EP 0 770 375, 1997.
English language Derwent abstract of JP 02-19576, 1990.
English language Derwent abstract of JP 05-163124, 1993.
XP002295406 of Izvestiya Vysshlkh Uchebnykh Zavedenii, Khimii I Khimlcheskol Tekhnologii, 2001, 44(4), 3-6.
XP002295405 of Voprosy Khimii I Khimicheskol Tekhnologii, 1987(84), 21-24.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to novel N-alkylamino secondary para-phenylenediamines; a composition for dyeing keratin fibers, for example, human keratin fibers such as the hair, comprising, in a medium suitable for dyeing, at least one such N-alkylamino secondary para-phenylenediamine; a process for dyeing keratin fibers comprising applying this composition; and the uses of this composition in the form of a dyeing "kit".

28 Claims, No Drawings

OTHER PUBLICATIONS

XP002295409 of Wuhan Daxue Xuebao, Ziran Kexueban, 1995, 41(6), 665-671.

Jacobs et al. "Unsymmetrical Derivatives of Aromatic Diamines." J. Am. Chem. Soc. 1917, 39(7), 1447-1465.

Orelli et al. "Synthesis and Properties of 1-Aryl-2-alkyl-1,4,5,6-tetrahydropyrimidines." J. Heterocycl. Chem. 1999, 36(1), 105-112.

Jani et al. "Synthesis of some Aminoacetamide Derivatives." J. Indian. Chem. Soc. 1990, 67, 602-603.

Gilman et al. "An Extension of the Smiles Rearrangement. The Displacement of an Aromatic Amide Group by an Amine Nitrogen." J. Org. Chem. 1973, 38(2), 373-377.

Stubbins et al. "Synthetic Analgesics I: N-(2-Dialkylaminoethyl)-2-phenylacetanilides." J. Pharm. Sci. 1966(55), 1093-1096.

He et al. "Studies on Organophosphorus Heterocycles Part IV. The Reaction of Lawesson's Reageant with Glycinamides, Synthesis and Herbicidal Activity of 1,3,2-Diazaphospholidin-4-thione-2-sulfides." Phosphorus, Sulfur Silicon Relat. El. 1997(129), 111-120.

Massa et al. "Spiro-[4H-Pyrrolo[1,2-a][1,4]benzodiazepine-4,4'-piperidine] Derviatives as Potential Nootropic Agents: A Simple One-Pot Synthesis." Synth. Commun. 1990, 20(22), 3537-3543.

Orelli et al. "Selective Monoformylation of 1,3-Diaminopropane Derivatives." Synth. Commun. 1999, 29, 1819-1933.

Kotsuki et al. "High Pressure Organic Chemistry; XII. A Convenient Synthesis of Aromatic Amines from Activated Aromatic Fluorides." Synthesis 1990 (12), 1147-1148.

\* cited by examiner

N-ALKYLAMINO SECONDARY PARA-PHENYLENEDIAMINE, COMPOSITION FOR DYEING KERATIN FIBERS COMPRISING SUCH A PARA-PHENYLENEDIAMINE, PROCESSES USING THIS COMPOSITION AND USES THEREOF

This application claims benefit of U.S. Provisional Application No. 60/569,645, filed May 11, 2004, and French Application No. 04/02022, filed Feb. 27, 2004, which are incorporated herein by reference.

The present disclosure relates to a novel family of N-alkylamino secondary para-phenylenediamines and their use for dyeing keratin fibers, for example, human keratin fibers, such as the hair.

It is known practice to dye keratin fibers, such as human hair, with dye compositions comprising oxidation dye precursors, such as ortho- or para-phenylenediamines, ortho- or para-aminophenols, and heterocyclic compounds, which are generally referred to as oxidation bases. These oxidation bases, are colorless or weakly colored compounds which, when combined with oxidizing products, may give rise to colored compounds by a process of oxidative condensation.

It is also known that the shades obtained with these oxidation bases may be varied by combining them with couplers or coloration modifiers. The couplers or coloration modifiers are chosen, for example, from aromatic meta-diaminobenzenes, meta-aminophenols, meta-diphenols and certain heterocyclic compounds, such as indole compounds.

The variety of molecules used as oxidation bases and couplers makes it possible to obtain a wide range of colors.

The "permanent" coloration obtained using these oxidation dyes should moreover satisfy a certain number of requirements. For example, it should have no toxicological drawbacks and it should allow shades of the desired intensity to be obtained and have good resistance to external agents such as light, bad weather, washing, permanent waving, perspiration and rubbing.

The dyes should also allow white hairs to be covered and they should be as unselective as possible, i.e., they should allow the smallest possible differences in coloration to be produced over the entire length of the same keratin fiber, which is generally differently sensitized (i.e., damaged) between its end and its root.

The present disclosure relates to novel compositions for dyeing keratin fibers, for example, human keratin fibers, such as the hair, which are capable of giving strong, aesthetic and sparingly selective colorations in varied shades, which may show good resistance to the various attacking factors to which the fibers may be subjected, by using at least one N-alkylamino secondary para-phenylenediamine.

In addition, these compositions have a good toxicological profile.

Disclosed herein are a family of N-alkylamino secondary para-phenylenediamines, processes for synthesizing them and their use for dyeing keratin fibers, for example, human keratin fibers, such as the hair.

Further disclosed herein are a composition comprising at least one N-alkylamino secondary para-phenylenediamine, dyeing processes using this composition, the uses of this composition for dyeing keratin fibers, for example, human keratin fibers, such as the hair, and multi-compartment devices or dye "kits".

The composition disclosed herein makes it possible, for example, to obtain very powerful, sparingly selective and fast, such as light-fast, dyeing of keratin fibers, while at the same time avoiding the degradation of these fibers.

Other characteristics, aspects, objects and advantages of the present disclosure will emerge even more clearly on reading the description and the examples that follow.

In the context of the present disclosure, the term "alkyl" means a linear or branched $C_1$-$C_{10}$ radical, chosen, for example, from the following linear or branched radicals: methyl, ethyl, propyl, butyl, pentyl, hexyl, octyl, etc.

The novel N-alkylamino secondary para-phenylenediamines as disclosed herein are compounds of formula (I):

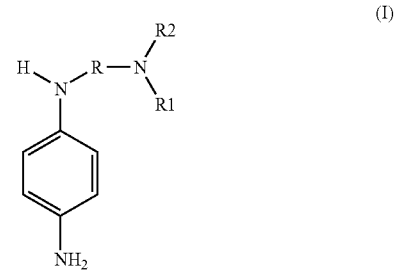

wherein:

radicals $R_1$ and $R_2$, which may be identical or different, are each chosen from a hydrogen atom, alkyl groups, monoalkylaminocarbonyl groups and dialkylamino-carbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one atom chosen from nitrogen and oxygen atoms, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen atoms, then the radicals $R_1$ and $R_2$ are not chosen from one of the following couples: two hydrogen atoms; two alkyl groups; and a hydrogen atom and an alkyl group, and with the proviso that the compound of formula (I) is not 4-[4-(piperidinyl)butylamino]aminobenzene, N-[3-(4-methylpiperazin-1-yl)propyl]benzene-1,4-diamine, or 4-[2-(piperidinyl)ethylamino]aminobenzene.

For example, $R_1$ is a hydrogen atom, $R_2$ is as defined above; or the radicals $R_1$ and $R_2$ form, together with the nitrogen on which they are substituent, a saturated 5- or 6-membered ring optionally interrupted with at least one nitrogen atom or with at least one carbonyl functional group, and optionally substituted with at least one alkyl group.

In one embodiment, $R_1$ and $R_2$ form, together with the nitrogen on which they are substituent, a saturated 5- or 6-membered ring optionally interrupted with at least one nitrogen atom or with at least one carbonyl functional group, and optionally substituted with a $C_1$-$C_3$ alkyl group.

In another embodiment, the radical R is a linear $C_1$-$C_7$ such as a linear $C_1$-$C_3$ alkylene radical.

In yet another embodiment, the radical R is unsubstituted or is interrupted with at least one atom chosen from nitrogen and oxygen.

The compounds of formula (I) may be in free form or in the form of one or more salts, such as the acid addition salts, chosen, for example, from hydrochlorides, hydrobromides, sulfates, citrates, succinates, tartrates, lactates, tosylates, benzenesulfonates, phosphates and acetates.

A number of exemplary compounds of formula (I) are given in the table below:

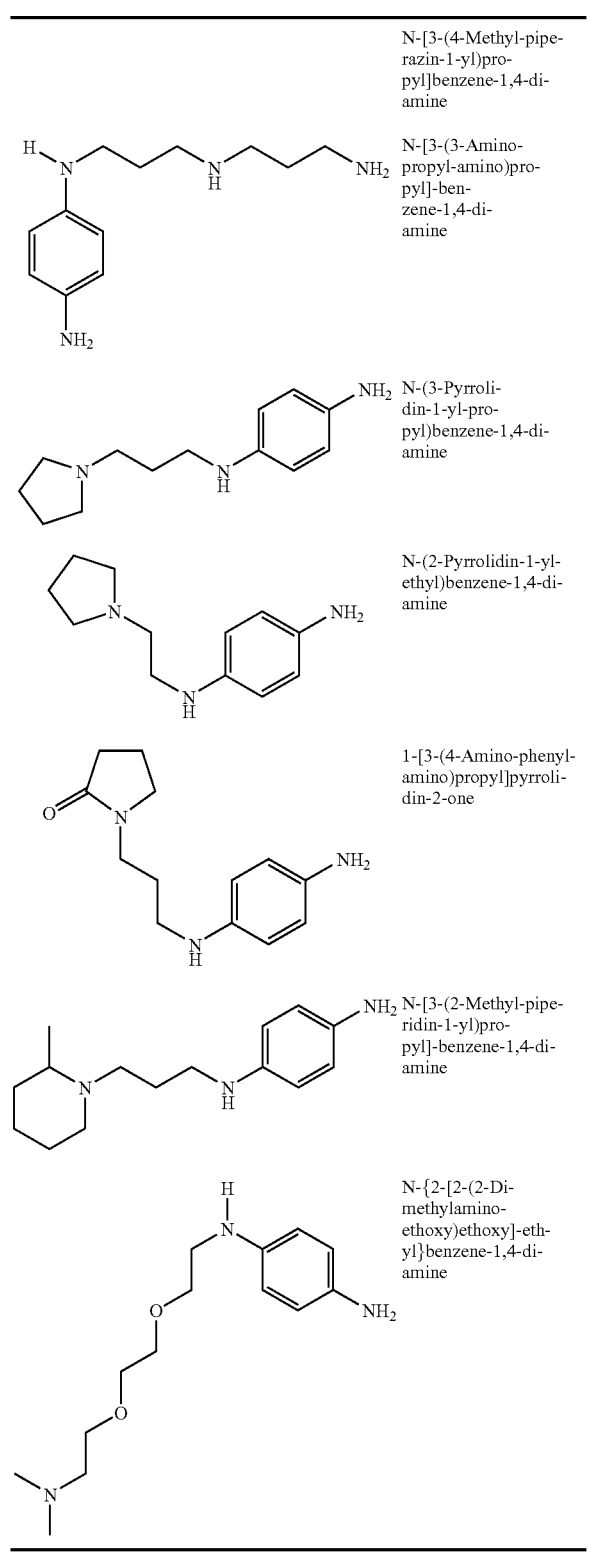

| | |
|---|---|
| | N-[3-(4-Methyl-piperazin-1-yl)propyl]benzene-1,4-diamine |
| | N-[3-(3-Aminopropyl-amino)propyl]-benzene-1,4-diamine |
| | N-(3-Pyrrolidin-1-yl-propyl)benzene-1,4-diamine |
| | N-(2-Pyrrolidin-1-yl-ethyl)benzene-1,4-diamine |
| | 1-[3-(4-Amino-phenylamino)propyl]pyrrolidin-2-one |
| | N-[3-(2-Methyl-piperidin-1-yl)propyl]-benzene-1,4-diamine |
| | N-{2-[2-(2-Dimethylamino-ethoxy)ethoxy]-ethyl}benzene-1,4-diamine |

The compounds of formula (I) disclosed herein may generally be prepared according to a method comprising:
 synthesis of a 4-(N-alkylamino)nitrobenzene compound by nucleophilic substitution of the halogen of a para-halonitrobenzene with a diamine of formula $R_1R_2NRNH_2$ (wherein $R_1$, $R_2$ and R are as defined above) in the presence of a base,
 reduction of the nitro group of the 4-(N-alkylamino)nitrobenzene compound obtained to give the compound of formula (I):

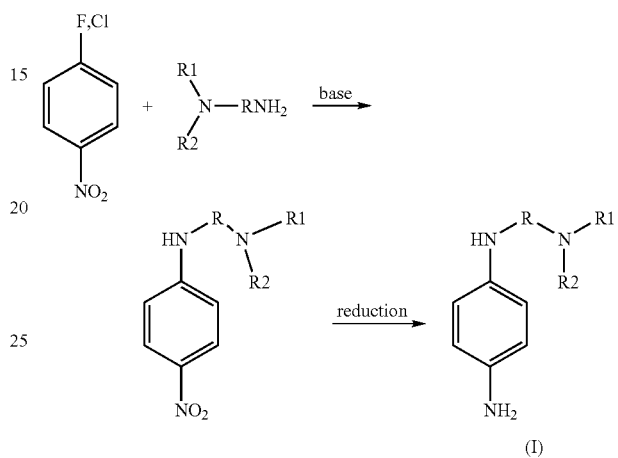

The first synthetic reaction is described in documents Synthesis 1990 (12), 1147-1148 and Synth. Commun. 1990, 20(22), 3537-3543.

The second reaction is a standard reduction reaction, carried out for example by performing a hydrogenation reaction via heterogeneous catalysis in the presence of Pd/C, Pd(II)/C or Raney Nickel, or alternatively by performing a reduction reaction with a metal, for example, with zinc, iron, tin, etc. (Advanced Organic Chemistry, $4^{th}$ edition, 1992, J. March, Wiley Interscience; Reduction in Organic Chemistry, M. Hudlicky, 1983, Ellis Honwood series Chemical Science).

A second synthetic route may be represented schematically as follows:

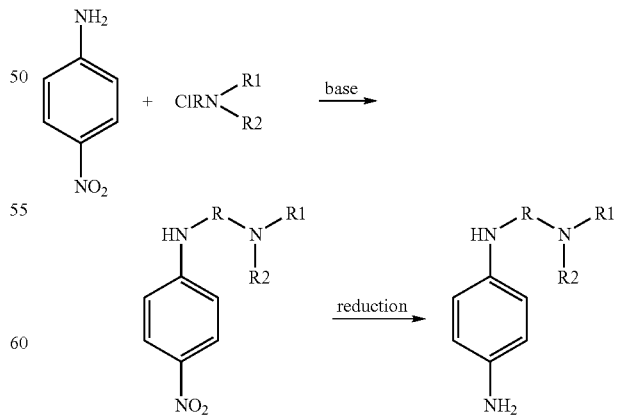

$1^{st}$ reaction: reaction inspired by J. Indian. Chem. Soc. 1990, 67, 602-603 or by Synth. Commun. 1999, 29, 1819-1933

$2^{nd}$ reaction: standard reduction reaction, which is performed as outlined in the general method above.

The present disclosure also relates to the nitro compounds of formula (II) and to processes for preparing the secondary para-phenylenediamine compounds of formula (I), comprising performing a reduction reaction of the corresponding nitro compound, wherein the "corresponding nitro compound" is the compound of formula (I) in which the amino group para to the group $NHRNR_1R_2$ is replaced with a nitro group.

These compounds are of the formula (II):

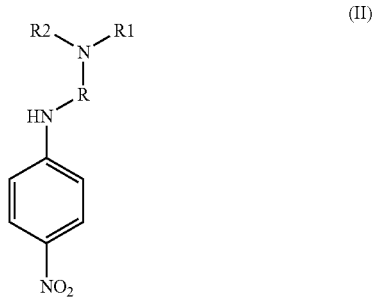

wherein:

radicals $R_1$ and $R_2$, which may be identical or different, are each chosen from a hydrogen atom, alkyl groups, monoalkylaminocarbonyl groups and dialkylamino-carbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group.

The present disclosure also relates to the uses of the compounds of general formula (I) disclosed herein for dyeing keratin fibers, for example, human keratin fibers, such as the hair. For example, the compounds of formula (I) that may be used include those wherein the radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a 5- or 6-membered saturated ring optionally interrupted with at least one entity chosen from a nitrogen atom and a carbonyl functional group, and optionally substituted with at least one alkyl group, the radical R is a linear or branched $C_1$-$C_{10}$ alkylene radical optionally interrupted with at least one atom chosen from nitrogen and oxygen atoms, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen, then the radicals $R_1$ and $R_2$ are not chosen from one of the following couples: two hydrogen atoms; two alkyl groups; and a hydrogen atom and an alkyl group.

The present disclosure also relates to a cosmetic composition for dyeing keratin fibers, for example, human keratin fibers such as the hair, comprising, in a medium suitable for dyeing, at least one compound of formula (I) wherein the radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a 5- or 6-membered saturated ring optionally interrupted with at least one entity chosen from a nitrogen atom and a carbonyl functional group, and optionally substituted with at least one alkyl group, the radical R is a linear or branched $C_1$-$C_{10}$ alkylene radical optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylamino-carbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group.

The present disclosure also relates to a cosmetic composition for dyeing keratin fibers, for example, human keratin fibers, such as the hair, comprising, in a medium suitable for dyeing, at least one compound of formula (I) and at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The present disclosure also relates to the use of a cosmetic composition for dyeing keratin fibers, for example, human keratin fibers, such as the hair, wherein the composition comprises, in a medium suitable for dyeing, at least one compound of formula (I), wherein:

the radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a 5- or 6-membered saturated ring optionally interrupted with at least one entity chosen from a nitrogen atom and a carbonyl functional group, and optionally substituted with at least one alkyl group, the radical R is a linear or branched $C_1$-$C_{10}$ alkylene radical optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylamino-carbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group.

The at least one compound of formula (I) is present in an amount ranging, for example, from 0.0001% to 20% by weight, such as from 0.005% 6% by weight, relative to the total weight of the composition.

The medium suitable for dyeing comprises, for example, water or a mixture of water and at least one organic solvent, chosen, for example, from branched and unbranched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol, and also aromatic alcohols, for instance benzyl alcohol or phenoxyethanol, and mixtures thereof.

The cosmetic composition further, for example, comprises at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The at least one cosmetic adjuvant is generally present in an amount ranging, for example, from 0.01% to 20% by weight relative to the total weight of the composition.

The composition disclosed herein may further comprises at least one additional oxidation base other than the compounds of formula (I). The composition disclosed herein may also comprise at least one coupler.

The at least one coupler may be chosen, for example, from meta-phenylenediamines, meta-aminophenols, meta-diphenols, naphthalene-based couplers and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxy-pyridine, 6-hydroxybenzomorpholine, 3,5-diamino-2,6-dimethoxypyridine, 1-N-(βhydroxyethyl)amino-3,4-methylenedioxybenzene and 2,6-bis(β-hydroxyethylamino)toluene, and the addition salts thereof.

Generally, the at least one coupler is present in an amount ranging, for example, from 0.0001% to 20% by weight, such as from 0.005% to 6% by weight, relative to the total weight of the composition.

The at least one additional oxidation base other than the compounds of formula (I) may be chosen, for example, from para-phenylenediamines, bis(phenyl)alkylenediamines, para-aminophenols, ortho-aminophenols and heterocyclic bases, and the addition salts thereof.

Among the para-phenylenediamines, mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-2-methyl-N,N-bis(β-hydroxyethyl)aniline, 4-amino-2-chloro-N,N-bis(β-hydroxyethyl) aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-di-hydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylene-diamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenylamino)hexan-1-ol, and the acid addition salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-α-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the acid addition salts thereof may, for example, be used.

Among the bis(phenyl)alkylenediamines, mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylene-diamine, N,N'-bis(ethyl)-N,N'-bis(4'-amino-3'-methylphenyl) ethylenediamine and 1,8-bis(2,5-diaminophenoxy)-3,6-dioxaoctane, and the acid addition salts thereof.

Among the para-aminophenols, mention may be made, for example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl] 2-methylphenol and bis(5'-amino-2'-hydroxy)phenylmethane and the acid addition salts thereof.

Among the ortho-aminophenols, mention may be made, for example, of 2-aminophenol, 2-amino-5-methylphenol, 2-amino-6-methylphenol, and 5-acetamido-2-aminophenol, and the acid addition salts thereof.

Among the heterocyclic bases, mention may be made, for example, of pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, and 3,4-diaminopyridine, and the acid addition salts thereof.

Other pyridine oxidation bases that are useful herein include, for example, the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and the acid addition salts thereof.

Among the pyrimidine derivatives, mention may be made of the compounds described, for example, in patents DE 2 359 399; JP 88 169 571; JP 05 63 124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine and the addition salts thereof and the tautomeric forms thereof, when a tautomeric equilibrium exists.

Among the pyrazole derivatives, mention may be made, for example, of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyra-zole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

The at least one additional oxidation base is present in an amount ranging, for example, from 0.0001% to 20% by weight, such as from 0.005% to 6% by weight, relative to the total weight of the composition.

In general, the addition acid salts that can be used for the oxidation bases and the couplers are chosen, for example, from hydrochlorides, hydrobromides, sulfates, citrates, succinates, tartrates, lactates, tosylates, benzenesulfonates, phosphates and acetates.

The dye composition as disclosed herein may also comprise at least one direct dye, which may be chosen, for example, from neutral, acidic and cationic nitrobenzene dyes, neutral, acidic and cationic azo direct dyes, neutral, acidic and cationic quinone such as anthraquinone direct dyes, azine direct dyes, methine, azomethine, triarylmethane and indoamine direct dyes, and natural direct dyes. In one embodiment, the composition as disclosed herein comprises at least one dye chosen from cationic direct dyes and natural direct dyes.

Among the cationic direct dyes that may be used herein, mention may be made, for example, of the cationic azo direct dyes described in patent applications WO 95/15144, WO 95/01772 and EP 714 954.

Among these compounds, mention may be made, for example, of the following dyes:

1,3-dimethyl-2-[[4-(dimethylamino)phenyl]azo]1H-imidazolium chloride, 1,3-dimethyl-2-[(4-aminophenyl)azo]1H-imidazolium chloride, and 1-methyl-4-[(methylphenylhydrazono)methyl]pyridinium methyl sulfate.

Among the natural direct dyes that may be used herein, mention may be made, for example, of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions comprising at least one of these natural dyes such as henna-based poultices or extracts.

The at least one direct dye is present in an amount ranging, for example, from 0.001% to 20% by weight, such as from 0.005% to 10% by weight, relative to the total weight of the composition.

A person skilled in the art will take care to select the at least one adjuvant, the at least one additional oxidation base, the at least one coupler, and the at least one direct dye such that the advantageous properties intrinsically associated with the dye composition disclosed herein are not, or are not substantially, adversely affected by the envisaged addition(s).

The pH of the dye composition disclosed herein ranges generally from 3 to 12, such as from 5 to 11. The pH may be adjusted to the desired value by adding at least one acidifying agent and/or at least one basifying agent usually used in the dyeing of keratin fibers, or alternatively using standard buffer systems.

Among the at least one acidifying agents that may be mentioned, examples include mineral or organic acids other than carboxylic diacids, for instance hydrochloric acid, orthophosphoric acid, sulfuric acid, carboxylic acids, for instance acetic acid, tartaric acid, citric acid and lactic acid, and sulfonic acids.

Among the at least one basifying agents that may be mentioned, examples include aqueous ammonia, alkali metal carbonates, alkanolamines such as monoethanolamine, diethanolamine and triethanolamine and also derivatives thereof, sodium hydroxide, potassium hydroxide and the compounds of formula:

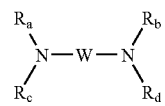

wherein W is a propylene residue optionally substituted with at least one hydroxyl group or a $C_1$-$C_4$ alkyl radical; $R_a$, $R_b$, $R_c$ and $R_d$, which may be identical or different, are each chosen from a hydrogen atom and $C_1$-$C_4$ alkyl and $C_1$-$C_4$ hydroxyalkyl radicals.

The cosmetic composition as disclosed herein may be in various forms, such as in the form of liquids, creams or gels, or in any other form that is suitable for dyeing keratin fibers, such as human hair.

The present disclosure relates to a process comprising applying to keratin fibers the composition as defined above for a time that is sufficient to develop the desired coloration, in the presence of at least one oxidizing agent, wherein the at least one oxidizing agent is applied before, simultaneously with or after the application of the composition. The color may be developed at acidic, neutral or alkaline pH and the at least one oxidizing agent may be added to the composition disclosed herein just at the time of use, or it may be used starting with an oxidizing composition comprising it, wherein the oxidizing composition is applied simultaneously with or sequentially to the composition disclosed herein.

In one embodiment, the composition disclosed herein is mixed, such as at the time of use, with a composition comprising, in a medium suitable for dyeing, at least one oxidizing agent, wherein the at least one oxidizing agent is present in an amount sufficient to develop a coloration. In this embodiment, a ready-to-use composition is provided, which is a mixture of a composition disclosed herein with at least one oxidizing agent chosen, for example, from hydrogen peroxide, urea peroxide, alkali metal bromates, persalts, peracids and oxidase enzymes. The mixture obtained, in the form of a ready-to-use composition, is then applied to the keratin fibers for a time that is sufficient to develop the desired coloration. After an action time of from 3 to 50 minutes such as from 5 to 30 minutes, the keratin fibers are rinsed, washed with a shampoo, rinsed again and then dried.

The at least one oxidizing agent is chosen from oxidizing agents conventionally used for the oxidation dyeing of keratin fibers chosen, for example, from hydrogen peroxide, urea peroxide, alkali metal bromates, persalts such as perborates and persulfates, peracids and oxidase enzymes, among which mention may be made, for example, of peroxidases, two-electron oxidoreductases such as uricases, and four-electron oxygenases, for instance laccases. In one embodiment, hydrogen peroxide is used.

The oxidizing composition may also comprise at least one adjuvant chosen from various adjuvants conventionally used in hair dye compositions and as defined above.

The pH of the oxidizing composition comprising the at least one oxidizing agent is such that, after mixing with the dye composition, the pH of the resulting composition applied to the keratin fibers ranges, for example, from 3 to 12, such as from 5 to 11. The pH may be adjusted to the desired value using at least one acidifying agent and/or at least one basifying agent, which are usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, such as human hair.

Further disclosed herein is a multi-compartment device or dyeing "kit", comprising a first compartment comprising the dye composition defined above and a second compartment comprising an oxidizing composition. This device may be equipped with an applicator for applying the desired mixture to the hair, such as the devices described in patent FR-2 586 913.

Using this device, it is possible to dye keratin fibers via a process that comprises mixing a dye composition disclosed herein with at least one oxidizing agent as defined above, and applying the mixture obtained to the keratin fibers for a time sufficient to develop the desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The examples that follow serve to illustrate the present disclosure without, however, being limiting in nature.

EXAMPLES OF SYNTHESIS

Example 1

Synthesis of N-[3-(3-aminopropylamino)propyl] benzene-1,4-diamine tetrahydrochloride (2)

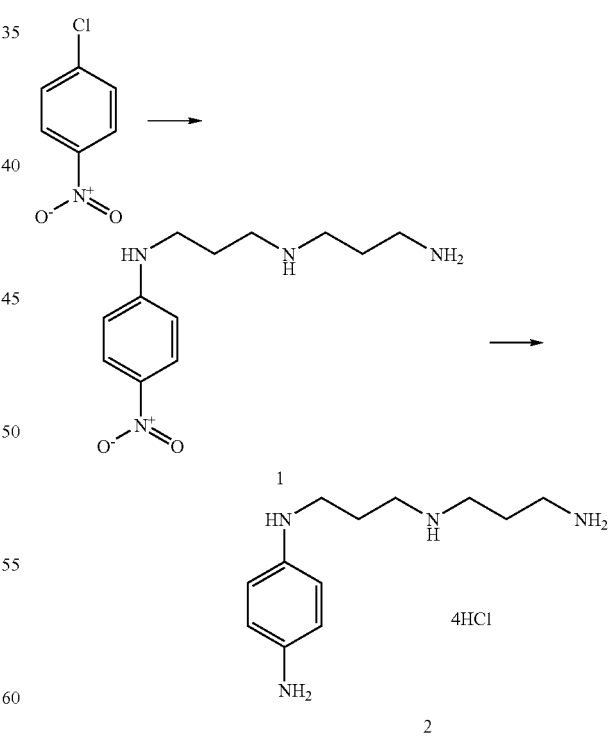

Step 1: Preparation of N-(3-aminopropyl)-N'-(4-nitrophenyl)propane-1,3-diamine (1)

105 g (0.8 mol) of N-1-(3-aminopropyl)propane-1,3-diamine were heated in a boiling water bath, and a warm solution of p-chloronitrobenzene (31.5 g, 0.2 mol) in 35 ml of pyridine was then added thereto over 1 hour, and heating was continued for 3 hours. When the reaction was complete, the medium was poured into 1 L of ice-cold water. The product was left to crystallize slowly at 0° C., and the yellow solid formed was then filtered off by suction and washed with ice-cold water, and then dried at 40° C. over $P_2O_5$. The product obtained (37.3 g) was recrystallized from 70 ml of acetonitrile to give 26.2 g of crystals, which were recrystallized again from 40 ml of acetonitrile. 19.9 g of monohydrate product were isolated (melting point=64° C.), and subject to the following elemental analyses:

|   | THEORY, $H_2O$ | FOUND |
|---|---|---|
| C | 53.32 | 53.30 |
| H | 8.20 | 8.11 |
| N | 20.73 | 20.76 |
| O | 17.76 | 18.08 |

Step 2: Preparation of N-[3-(3-aminopropylamino)propyl]-benzene-1,4-diamine tetrahydrochloride (2)

A mixture of zinc powder (32 g), ammonium chloride (1.3 g), water (6.8 ml) and 96% ethanol (65 ml) was refluxed in a boiling water bath. The derivative N-(3-aminopropyl)-N'-(4-nitrophenyl)propane-1,3-diamine (1) (16.5 g; $6.5 \times 10^{-2}$ mol) was added portionwise and heating was continued until the reaction medium was decolorized. The medium was filtered while hot and the filtrate was recovered into 50 ml of cold 7N hydrochloric ethanol. The zinc was washed with a minimum amount of boiling ethanol and the filtrate was cooled to 0° C. The white crystals formed were filtered off by suction, washed with ethyl ether and dried under vacuum at 45° C. over $P_2O_5$/KOH to give 21.1 g of tetrahydrochloride products.

|   | THEORY, 4HCl | FOUND |
|---|---|---|
| C | 39.15 | 39.14 |
| H | 7.12 | 7.05 |
| N | 15.22 | 15.13 |
| Cl | 38.52 | 38.54 |

The proton NMR and mass spectra were in accordance with the expected structure of the product.

Example 2

Synthesis of 2-(4-aminophenylamino)acetamide dihydrochloride (4)

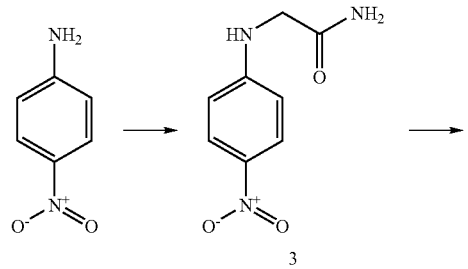

-continued

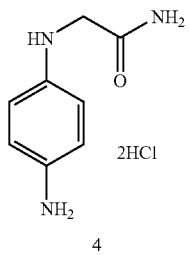

Step 1: Preparation of 2-(4-nitrophenylamino)acetamide (3)

A mixture of p-nitroaniline (55.2 g, 0.4 mol), calcium carbonate (80 g) and chloroacetamide (149.6 g, 1.6 mol) in 350 ml of water/ethanol (1/1) was refluxed for 42 hours. The resulting mixture was filtered while hot and allowed to cool, and the crystals were filtered off by suction, reslurried in water and then washed with absolute ethanol. After drying, 87.9 g of crude product were obtained. After two recrystallizations from acetonitrile, 45.3 g of pure product were obtained (melting point=178° C.).

Step 2: Preparation of 2-(4-aminophenylamino)acetamide dihydrochloride (4)

29.3 g (0.15 mol) of 2-(4-nitrophenylamino)acetamide (3) and 500 ml of absolute ethanol were placed in a 1 L stainless-steel hydrogenator, and 1 g of Pd/C (10% water) was added.

The mixture was placed under a pressure of 10 bar of hydrogen at 50° C. for 4 hours. After filtering off the catalyst, the filtrate was acidified with 84 ml (0.36 mol) of 4.3N hydrochloric ethanol. This mixture was diluted with 84 ml of isopropyl ether, and the precipitate formed was filtered off by suction, washed with isopropyl ether and then dried at 55° C. The mass of the product obtained was 12.2 g.

|   | THEORY, 2HCl | FOUND |
|---|---|---|
| C | 40.33 | 32.49 |
| H | 5.46 | 7.22 |
| N | 17.65 | 17.50 |
| Cl | 29.78 | 30.12 |

The proton NMR and mass spectra were in accordance with the expected structure of the product.

Example 3

Synthesis of N-[3-(4-methylpiperazin-1-yl)propyl]benzene-1,4-diamine Dihydrochloride (10)

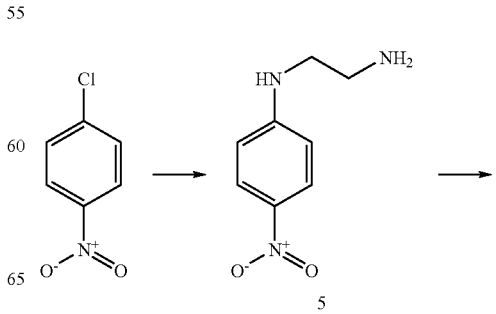

15

-continued

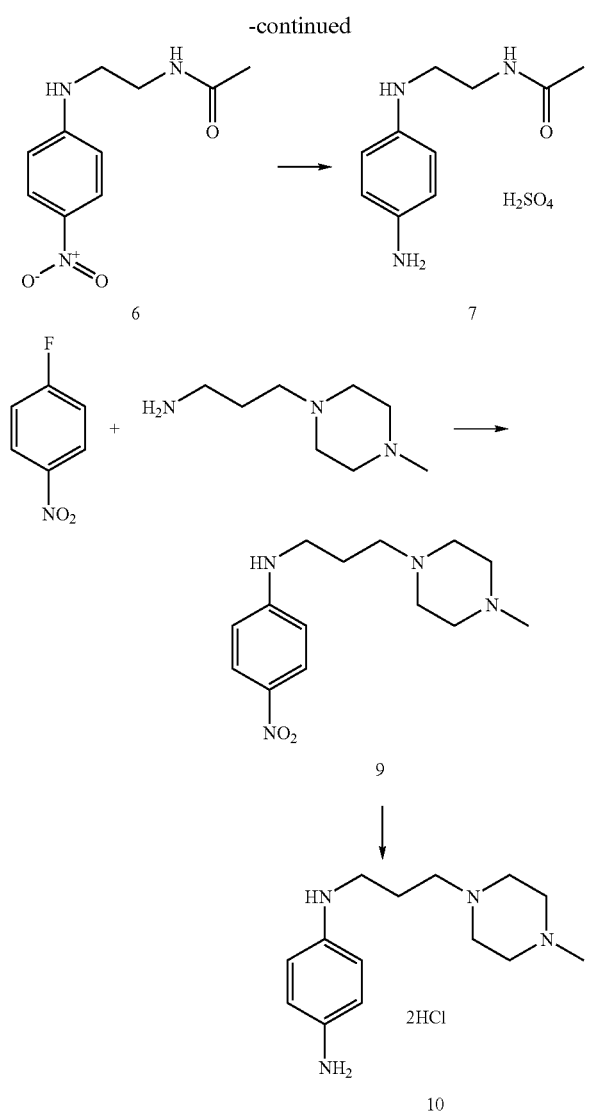

16

Example 4

Synthesis of
1-[3-(4-aminophenylamino)propyl]pyrrolidin-2-one
Dihydrochloride (12)

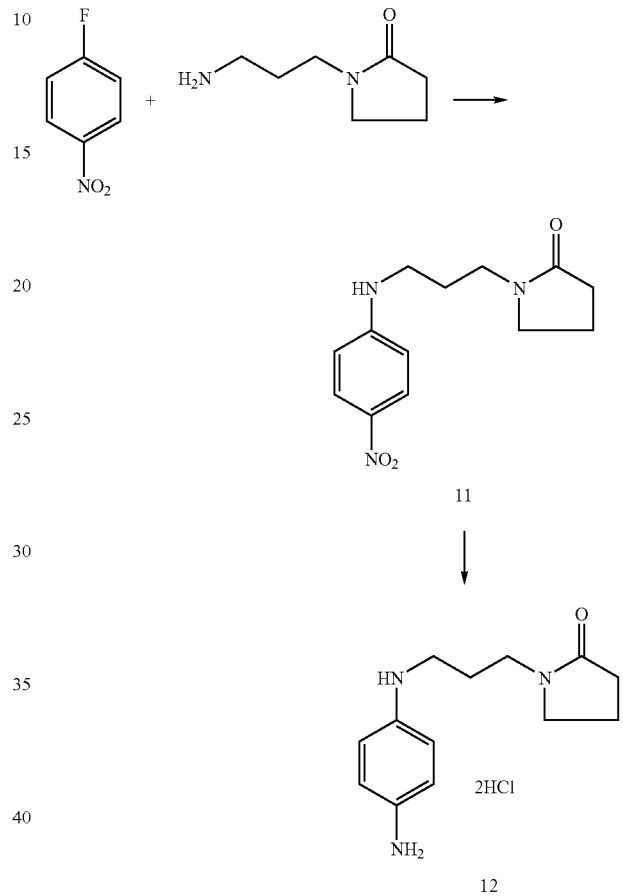

Step 1: Synthesis of N-[3-(4-methylpiperazin-1-yl)propyl]-4-nitro-1-aminobenzene (9)

2 g of 4-fluoronitrobenzene were added to a solution of 20 ml of N-methyl-pyrrolidine, 2.67 g of N-(3-aminopropyl)-N'-methylpiperazine and 2.35 g of $K_2CO_3$. The reaction medium was heated at 60° C. for 10 hours and, after cooling to room temperature, was then poured into a water and ice mixture. The yellow precipitate formed was filtered off, reslurried in water and then dried over $P_2O_5$. 3.22 g of N-[3-(4-methyl-piperazin-1-yl)propyl]-4-nitro-1-aminobenzene (9) were obtained.

Step 2: Synthesis of N-[3-(4-methylpiperazin-1-yl)propyl]benzene-1,4-diamine Dihydrochloride (10)

The N-[3-(4-methyl-piperazin-1-yl)propyl]-4-nitro-1-aminobenzene (9) obtained above was reduced with a boiling zinc/ammonium chloride/water/ethanol mixture. The corresponding amine was isolated in dihydrochloride form.

The proton NMR and mass spectra were in accordance with the expected structure of the product.

Step 1: Synthesis of 1-[3-(4-nitro-3-phenylamino)propyl]pyrrolidin-2-one (11)

2 g of 4-fluoronitrobenzene were added to a solution of 20 ml of N-methyl-pyrrolidinone, 2.41 g of N-(3'-aminopropyl)-2-pyrrolidinone and 1.72 g of triethylamine. The reaction medium was heated at 60° C. for 10 hours and, after cooling to room temperature, was then poured into a water and ice mixture. The yellow precipitate formed was filtered off, reslurried in water and then dried over $P_2O_5$. 2.8 g of 1-[3-(4-nitro-3-phenylamino)propyl]pyrrolidin-2-one (11) were obtained.

Step 2: Synthesis of 1-[3-(4-amino-3-phenylamino)propyl]pyrrolidin-2-one Dihydrochloride (12)

The 1-[3-(4-nitro-3-phenylamino)propyl]pyrrolidin-2-one (11) obtained above was reduced with a boiling zinc/ammonium chloride/water/ethanol mixture. The corresponding amine was isolated in dihydrochloride form.

The proton NMR and mass spectra were in accordance with the expected structure of the product.

Example 5

Synthesis of N-(3-pyrrolidin-1-ylpropyl)benzene-1,4-diamine Dihydrochloride (14)

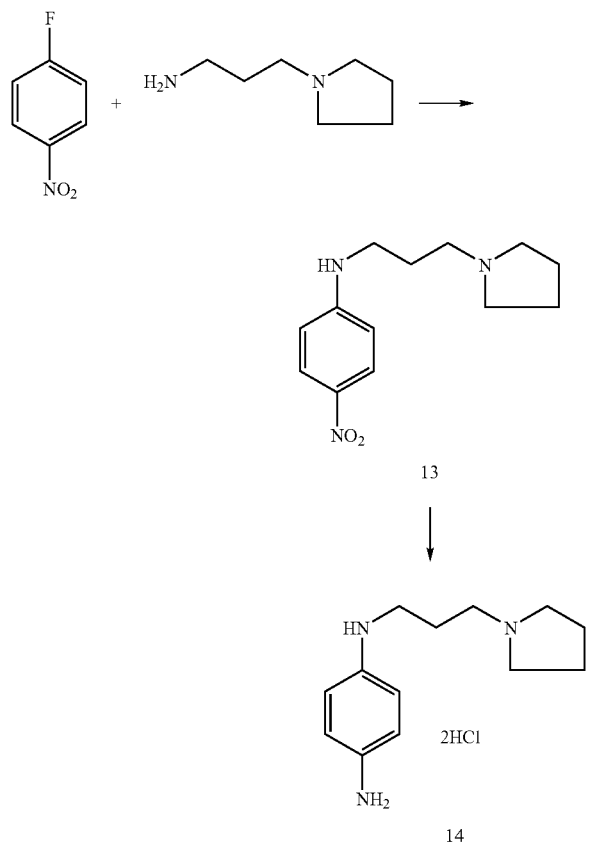

Step 1: Synthesis of N-(3-pyrrolidin-1-ylpropyl)-4-nitro-1-aminobenzene (13)

2 g of 4-fluoronitrobenzene were added to a solution of 20 ml of N-methyl-pyrrolidinone, 2.18 g of N-(3-aminopropyl)pyrrolidine and 2.35 g of $K_2CO_3$. The reaction medium was heated at 60° C. for 12 hours and, after cooling to room temperature, was then poured into a water and ice mixture. The yellow precipitate formed was filtered off, reslurried in water and then dried over $P_2O_5$. 3.3 g of N-(3-pyrrolidin-1-ylpropyl)-4-nitro-1-aminobenzene (13) were obtained.

Step 2: Synthesis of N-(3-pyrrolidin-1-ylpropyl)benzene-1,4-diamine Dihydrochloride (14)

The N-(3-pyrrolidin-1-ylpropyl)-4-nitro-1-aminobenzene (13) obtained above was reduced with a boiling zinc/ammonium chloride/water/ethanol mixture. The corresponding amine was isolated in dihydrochloride form.

The proton NMR and mass spectra were in accordance with the expected structure of the product.

Example 6

Synthesis of N-(3-pyrrolidin-1-ylethyl)benzene-1,4-diamine Dihydrochloride (16)

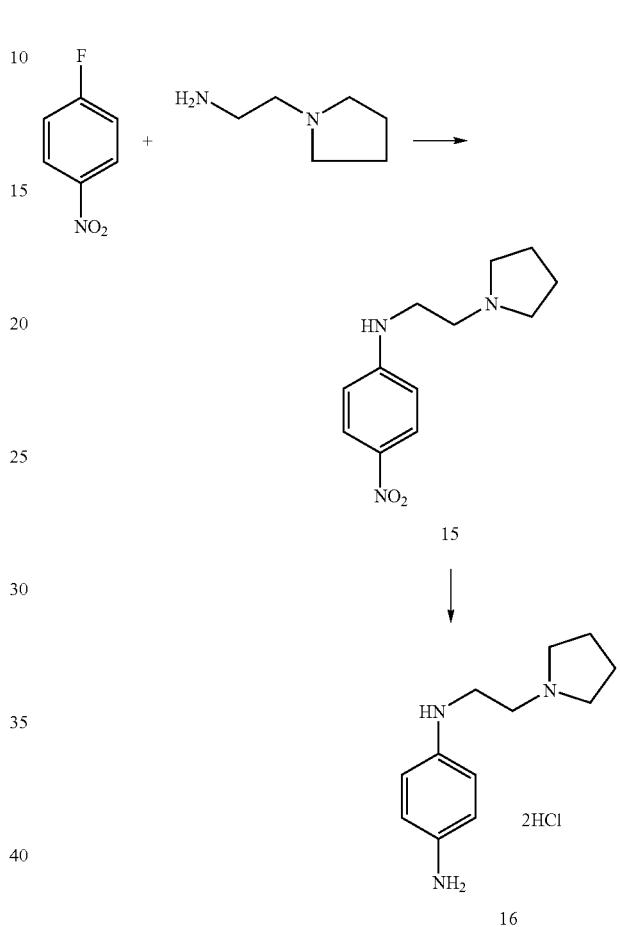

Step 1: Synthesis of N-(3-pyrrolidin-1-ylethyl)-4-nitro-1-aminobenzene (15)

2 g of para-fluoronitrobenzene were added to a solution of 20 ml of N-methyl-pyrrolidinone, 1.94 g of 2-(1-pyrrolidino)ethylamine and 2.35 g of $K_2CO_3$. The reaction medium was heated at 60° C. for 8 hours and, after cooling to room temperature, was then poured into a water and ice mixture. The yellow precipitate formed was filtered off, reslurried in water and then dried over $P_2O_5$. 2.5 g of N-(3-pyrrolidin-1-ylethyl)-4-nitro-1-aminobenzene (15) were obtained.

Step 2: Synthesis of N-(3-pyrrolidin-1-ylethyl)benzene-1,4-diamine Dihydrochloride (16)

The N-(3-pyrrolidin-1-ylethyl)-4-nitro-1-aminobenzene (15) obtained above was reduced with a boiling zinc/ammonium chloride/water/ethanol mixture. The corresponding amine was isolated in dihydrochloride form.

The proton NMR and mass spectra were in accordance with the expected structure of the product.

Example 7

Synthesis of N-[3-(2-methylpiperidin-1-yl)propyl]benzene-1,4-diamine Dihydrochloride (18)

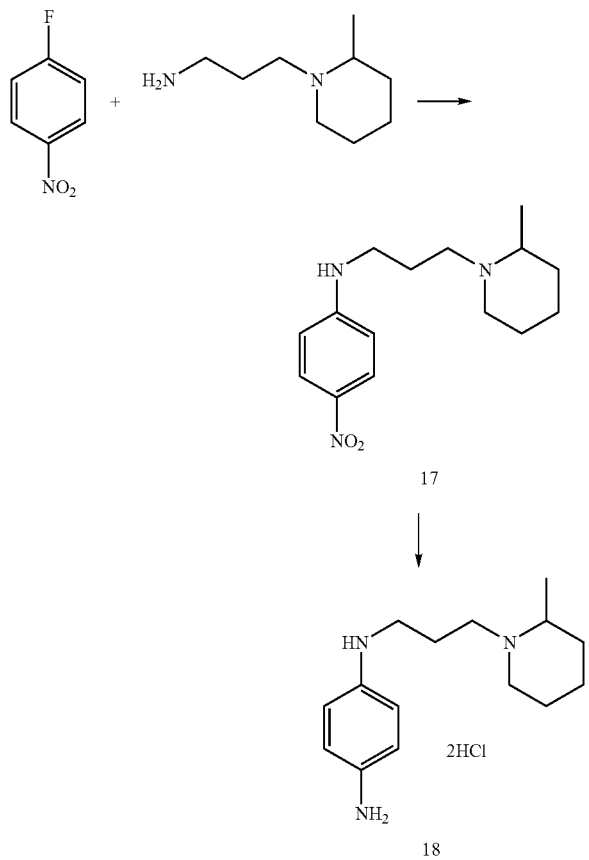

Step 1: Synthesis of N-[3-(2-Methylpiperidin-1-yl)propyl]-4-nitro-1-aminobenzene (17)

2 g of para-fluoronitrobenzene were added to a solution of 20 ml of N-methyl-pyrrolidinone, 1.65 g of 1-(3-aminopropyl)-2-pipecoline and 1.72 g of triethylamine. The reaction medium was heated at 60° C. for 8 hours and, after cooling to room temperature, was then poured into a water and ice mixture. The yellow precipitate formed was filtered off, reslurried in water and then dried over $P_2O_5$. 2.2 g of N-[3-(2-methyl-piperidin-1-yl)propyl]-4-nitro-1-aminobenzene (17) were obtained.

Step 2: Synthesis of N-[3-(2-methylpiperidin-1-yl)propyl]benzene-1,4-diamine Dihydrochloride (18)

The N-[3-(2-methylpiperidin-1-yl)propyl]-4-nitro-1-aminobenzene (17) obtained above was reduced with a boiling zinc/ammonium chloride/water/ethanol mixture. The corresponding amine was isolated in dihydrochloride form.

The proton NMR and mass spectra were in accordance with the expected structure of the product.

Example 8

Synthesis of N-(3-{2-[2-(3-aminopropoxy)ethoxy]ethoxy}-propyl)benzene-1,4-diamine Hydrochloride (20)

Step 1: Preparation of N-(3-{2-[2-(3-aminopropoxy)ethoxy]ethoxy}propyl)-N-(4-nitrophenyl)amine (19)

1.41 g (0.01 mol) of 1-fluoro-4-nitrobenzene and 1.62 ml (0.02 mol) of pyridine were introduced into a three-necked flask under nitrogen. 8.75 ml (0.04 mol) of 4,7,10-trioxatridecane-1,13-diamine were added dropwise with stirring. The mixture was heated to 70° C. After reaction for 24 hours, the reaction mixture was cooled and 40 ml of distilled water were then added with vigorous stirring. Next, the reaction mixture was extracted with dichloromethane, washed twice with water, dried over $MgSO_4$ and then evaporated under vacuum. The crude product, isolated in the form of a yellow oil comprising about 90% of expected mono-nitro derivative, was purified on a column of silica, eluting with ethyl acetate (to separate out the dinitro derivative), and then with methanol (to recover the expected mono-nitro derivative). 1.8 g of expected product (19) were obtained in the form of a dark yellow oil.

Step 2: Preparation of N-(3-{2-[2-(3-aminopropoxy)ethoxy]ethoxy}propyl)benzene-1,4-diamine Hydrochloride (20)

1.5 g of nitro derivative (19) prepared above and about 100 ml of methanol were introduced into a 200 ml autoclave (hydrogenator) equipped with a magnetic stirrer. The solution obtained was degassed with nitrogen. 0.4 g of palladium-on-charcoal (5% humidity, comprising 50% water) was added thereto. The reaction mixture was stirred, while flushing once with hydrogen, and hydrogen was then introduced to a pressure of about 5 bar. After reaction for 4 hours, the reactor was flushed with nitrogen and the reaction mixture was filtered quickly through Celite under a gentle pressure of nitrogen. The filtrate was recovered in a pre-cooled solution of methanol comprising about 3 equivalents of hydrogen chloride gas. It was rinsed several times with methanol under a stream of nitrogen. The solution thus obtained was concentrated and was then treated with ether. The product obtained, in the form of a pale pink paste, was stirred and then rinsed several times with acetonitrile and ether under nitrogen. 1.6 g of expected product (20) were isolated in the form of a slightly pink white powder.

The proton and $^{13}C$ NMR spectra and microanalysis spectra were in accordance with the expected structure of the product

EXAMPLES OF FORMULATION

Examples 1 to 6

Dye composition comprising 2-(4-aminophenyl-amino)acetamide Dihydrochloride (4)

Examples 1 to 3

Dyeing in Neutral Medium

The following dye compositions were prepared:

| | Example | | |
|---|---|---|---|
| | 1 | 2 | 3 |
| 2-(4-Amino-phenylamino)-acetamide, dichlorhydrate (4) | $10^{-3}$ mol | $10^{-3}$ mol | $10^{-3}$ mol |
| 1H-Indol-6-ol | $10^{-3}$ mol | | |
| 2-(2,4-Diamino-phenoxy)-ethanol, chlorhydrate | | $10^{-3}$ mol | |
| 3-Amino-2-chloro-6-methyl-phenol, chlorhydrate | | | $10^{-3}$ mol |
| Dye support (1) | (*) | (*) | (*) |
| Dmineralized water qs | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

\* A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | |
|---|---|---|---|
| | 1 | 2 | 3 |
| Shade observed | orange brown | grey | red |

Examples 4 to 6

Dyeing in Basic Medium

The following dye compositions were prepared:

| | Example | | |
|---|---|---|---|
| | 4 | 5 | 6 |
| 2-(4-Amino-phenylamino)-acetamide, dichlorhydrate (4) | $10^{-3}$ mol | $10^{-3}$ mol | $10^{-3}$ mol |
| 3,6-Dimethyl-1H-pyrazolo[5,1-c][1,2,4]triazole | $10^{-3}$ mol | | |
| 2-(2,4-Diamino-phenoxy)-ethanol, chlorhydrate | | $10^{-3}$ mol | |
| 3-Amino-2-chloro-6-methyl-phenol, chlorhydrate | | | $10^{-3}$ mol |

| | Example | | |
|---|---|---|---|
| | 4 | 5 | 6 |
| Dye support (2) | (\*) | (\*) | (\*) |
| Demineralized water qs | 100 g | 100 g | 100 g |

(\*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

\* A.M. means active material

At the time of use, each composition was mixed with an equal weight of 20-volume aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | |
|---|---|---|---|
| | 4 | 5 | 6 |
| Shade observed | chromatic red | violet-blue grey | violet-red |

Examples 7 to 16

Dye Composition Comprising 1-[3-(4-aminophenylamino)-propyl]pyrrolidin-2-one Dihydrochloride (12)

Examples 7 to 13

Dyeing in Neutral Medium

The following dye compositions were prepared:

| | Example | | | | | | |
|---|---|---|---|---|---|---|---|
| | 7 | 8 | 9 | 10 | 11 | 12 | 13 |
| 1-[3-(4-Aminophenylamino)-propyl]pyrrolidin-2-one dihydrochloride (12) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo-[5,1-c][1,2,4]triazole | | | | | $10^{-3}$ mol | | |

-continued

|  | Example | | | | | | |
|---|---|---|---|---|---|---|---|
|  | 7 | 8 | 9 | 10 | 11 | 12 | 13 |
| 2-(2,4-Diaminophenoxy)ethanol hydrochloride |  |  |  |  |  | $10^{-3}$ mol |  |
| 3-Amino-2-chloro-6-methylphenol hydrochloride |  |  |  |  |  |  | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| 96° ethyl alcohol | 20.8 g |
|---|---|
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

* A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| 96° ethyl alcohol | 20.8 g |
|---|---|
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

* A.M. means active material.

At the time of use, each composition was mixed with an equal weight of 20-volume aqueous hydrogen peroxide solution (6% by weight). A final pH of 9.5 was obtained.

|  | Example | | | | | | |
|---|---|---|---|---|---|---|---|
|  | 7 | 8 | 9 | 10 | 11 | 12 | 13 |
| Shade observed | brown | strong violet-grey | strong red-brown | strong red-brown | red-brown | strong blue-grey | strong blue-violet |

Examples 14 to 16

Dyeing in Basic Medium

The following dye compositions were prepared:

Each mixture obtained was applied to locks of grey hair comprising 90% white hairs. After an action time of 30 minutes, the locks were rinsed, washed with a standard shampoo, rinsed again and then dried.

The shades obtained are given in the table below:

|  | Example | | |
|---|---|---|---|
|  | 14 | 15 | 16 |
| 1-[3-(4-Aminophenylamino)propyl]-pyrrolidin-2-one dihydrochloride (12) | $10^{-3}$ mol | $10^{-3}$ mol | $10^{-3}$ mol |
| 5-Amino-2-methylphenol | $10^{-3}$ mol |  |  |
| 2-(2,4-Diaminophenoxy)ethanol hydrochloride |  | $10^{-3}$ mol |  |
| 3-Amino-2-chloro-6-methylphenol hydrochloride |  |  | $10^{-3}$ mol |
| Dye support (2) | (*) | (*) | (*) |
| Demineralized water qs | 100 g | 100 g | 100 g |

(*): dye support (2) pH 9.5

| | Example | | |
|---|---|---|---|
| | 14 | 15 | 16 |
| Shade observed | red-violet grey | strong blue | strong blue-violet |

Examples 17 to 28

Dye Composition Comprising N-(3-pyrrolidin-1-yl-propyl)benzene-1,4-diamine Dihydrochloride (14)

Examples 17 to 23

Dyeing in Neutral Medium

The following dye compositions were prepared:

| | Example | | | | | | |
|---|---|---|---|---|---|---|---|
| | 17 | 18 | 19 | 20 | 21 | 22 | 23 |
| N-(3-Pyrrolidin-1-ylpropyl)-benzene-1,4-diamine dihydrochloride (14) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

* A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | | | | | |
|---|---|---|---|---|---|---|---|
| | 17 | 18 | 19 | 20 | 21 | 22 | 23 |
| Shade observed | brown | red-violet grey | strong red-brown | red-brown | orange-brown | strong blue-grey | strong violet |

Examples 24 to 28

Dyeing in Basic Medium

The following dye compositions were prepared:

|  | Example | | | | |
|---|---|---|---|---|---|
|  | 24 | 25 | 26 | 27 | 28 |
| N-(3-Pyrrolidin-1-yl-propyl)benzene-1,4-diamine dihydrochloride (14) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 2-Amino-pyridin-3-ol | | $10^{-3}$ mol | | | |
| 3,6-Dimethyl-1H-pyrazolo-[5,1-c][1,2,4]triazole | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

* A.M. means active material.

At the time of use, each composition was mixed with an equal weight of 20-volume aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

|  | Example | | | | |
|---|---|---|---|---|---|
|  | 24 | 25 | 26 | 27 | 28 |
| Shade observed | red-violet | red | chromatic red | strong blue | strong violet |

Examples 29 to 37

Dye Composition Comprising N-(3-pyrrolidin-1-ylethyl)-benzene-1,4-diamine Dihydrochloride (16)

Examples 29 to 32

Dyeing in Neutral Medium

The following dye compositions were prepared:

|  | Example | | | |
|---|---|---|---|---|
|  | 29 | 30 | 31 | 32 |
| N-(3-Pyrrolidin-1-ylethyl)-benzene-1,4-diamine dihydrochloride (16) | $10^{-3}$ mol | $10^{-3}$ mol | $10^{-3}$ mol | $10^{-3}$ mol |
| 1H-Indol-6-ol | $10^{-3}$ mol | | | |
| 2-Aminopyridin-3-ol | | $10^{-3}$ mol | | |
| 2-(2,4-Diaminophenoxy)-ethanol hydrochloride | | | $10^{-3}$ mol | |
| 3-Amino-2-chloro-6-methylphenol hydrochloride | | | | $10^{-3}$ mol |
| Dye support (1) | (*) | (*) | (*) | (*) |
| Demineralized water qs | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

*A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | | |
|---|---|---|---|---|
| | 29 | 30 | 31 | 32 |
| Shade observed | strong red-brown | orange | strong blue-grey | red-violet |

Examples 33 to 37

Dyeing in Basic Medium

The following dye compositions were prepared:

| | Example | | | | |
|---|---|---|---|---|---|
| | 33 | 34 | 35 | 36 | 37 |
| N-(3-Pyrrolidin-1-yl-ethyl)benzene-1,4-diamine dihydrochloride (16) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 2-Aminopyridin-3-ol | | $10^{-3}$ mol | | | |
| 3,6-Dimethyl-1H-pyrazolo[5,1-c]-[1,2,4]triazole | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

* A.M. means active material.

At the time of use, each composition was mixed with an equal weight of 20-volume aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | | | |
|---|---|---|---|---|---|
| | 33 | 34 | 35 | 36 | 37 |
| Shade observed | red | orange | chromatic red | strong blue-violet | strong violet |

Examples 38 to 48

Dye Composition Comprising N-[3-(4-methyl-piperazin-1-yl)propyl]benzene-1,4-diamine Dihydrochloride (10)

Examples 38 to 44

Dyeing in Neutral Medium

The following dye compositions were prepared:

|  | Example | | | | | | |
|---|---|---|---|---|---|---|---|
|  | 38 | 39 | 40 | 41 | 42 | 43 | 44 |
| N-[3-(4-Methylpiperazin-1-yl)propyl]benzene-1,4-diamine dihydrochloride (10) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

*A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 38 | 39 | 40 | 41 | 42 | 43 | 44 |
| Shade observed | yellow-brown | strong red-violet grey | strong red-brown | red-brown | orange-brown | strong blue | strong blue-violet |

Examples 45 to 48

Dyeing in Basic Medium

The following dye compositions were prepared:

|  | Example | | | |
|---|---|---|---|---|
|  | 45 | 46 | 47 | 48 |
| N-[3-(4-Methylpiperazin-1-yl)propyl]benzene-1,4-diamine dihydrochloride (10) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)-ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

*A.M. means active material.

At the time of use, each composition was mixed with an equal weight of 20-volume aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | | |
|---|---|---|---|---|
| | 45 | 46 | 47 | 48 |
| Shade observed | red-grey | chromatic red | blue | strong blue-violet |

Examples 49 to 58

Dye Composition Comprising N-(3-pyrrolidin-1-yl-ethyl)benzene-1,4-diamine Dihydrochloride (16)

Examples 49 to 54

Dyeing in Neutral Medium

The following dye compositions were prepared:

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

*A.M. means active material.

At the time of use, each composition was mixed with an equal weight of 20-volume aqueous hydrogen peroxide solution (6% by weight). A final pH of 7 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

| | Example | | | | | |
|---|---|---|---|---|---|---|
| | 49 | 50 | 51 | 52 | 53 | 54 |
| Shade observed | brown | strong red-violet | strong brown | orange-brown | strong blue-grey | strong violet |

Examples 55 to 58

Dyeing in Basic Medium

The following dye compositions were prepared:

| | Example | | | | | |
|---|---|---|---|---|---|---|
| | 49 | 50 | 51 | 52 | 53 | 54 |
| N-(3-Pyrrolidin-1-ylethyl)-benzene-1,4-diamine dihydrochloride (16) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | |
| 5-Amino-2-methylphenol | | $10^{-3}$ mol | | | | |
| 1H-Indol-6-ol | | | $10^{-3}$ mol | | | |
| 3,6-Dimethyl-1H-pyrazolo[5,1-c]-[1,2,4]triazole | | | | $10^{-3}$ mol | | |
| 2-(2,4-Diaminophenoxy)-ethanol hydrochloride | | | | | $10^{-3}$ mol | |
| 3-Amino-2-chloro-6-methylphenol hydrochloride | | | | | | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

|  | Example | | | |
|---|---|---|---|---|
|  | 55 | 56 | 57 | 58 |
| N-(3-Pyrrolidin-1-yl-ethyl)benzene-1,4-diamine dihydrochloride (16) | $10^{-3}$ mol | $10^{-3}$ mol | $10^{-3}$ mol | $10^{-3}$ mol |
| Benzene-1,3-diol | $10^{-3}$ mol | | | |
| 5-Amino-2-methylphenol | | $10^{-3}$ mol | | |
| 2-(2,4-Diaminophenoxy)-ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5

| 96° ethyl alcohol | 20.8 g |
|---|---|
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ Alkyl polyglucoside as an aqueous 60% solution | 3.6 g A.M. |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% $NH_3$ | 2.94 g |

*A.M. means active material.

At the time of use, each composition was mixed with an equal weight of 20-volume aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

|  | Example | | | |
|---|---|---|---|---|
|  | 55 | 56 | 57 | 58 |
| Shade observed | brown | red-grey | strong blue-grey | Strong violet |

What is claimed is:

1. A compound, wherein the compound is an N-alkylamino secondary para-phenylenediamine of formula (I):

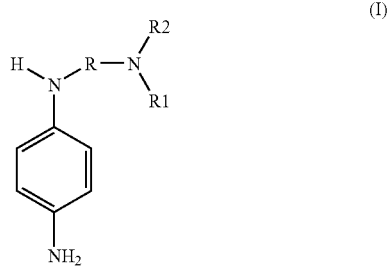

(I)

wherein:
radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one atom chosen from nitrogen and oxygen atoms, and optionally substituted with at least one group chosen from amino, monoalkylamino, dialkylamino, alkylcarbonyl, amido, monoalkylaminocarbonyl and dialkylamino-carbonyl groups, with the proviso that, when R is a linear or branched $C_1$-$C_{10}$ alkylene radical that is unsubstituted and not interrupted with at least one atom chosen from nitrogen and oxygen, then the radicals $R_1$ and $R_2$ are not chosen from one of the following couples: two hydrogen atoms; two alkyl groups; and a hydrogen atom and an alkyl group, and with the proviso that the compound is not 4-[4-(piperidinyl)butylamino]aminobenzene, N-[3-(4-methylpiperazin-1-yl)propyl]benzene-1,4-diamine, or 4-[2-(piperidinyl)ethylamino]-aminobenzene.

2. The compound according to claim 1, wherein $R_1$ is a hydrogen atom.

3. The compound according to claim 1, wherein $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group.

4. The compound according to claim 3, wherein $R_1$ and $R_2$ form, together with the nitrogen on which they are substituent, a saturated 5- or 6-membered ring interrupted with at least one entity chosen from a nitrogen atom and a carbonyl functional group, and optionally substituted with a $C_1$-$C_3$ alkyl group.

5. The compound according to claim 1, wherein R is a linear $C_1$-$C_7$ alkylene radical.

6. The compound according to claim 5, wherein R is unsubstituted or interrupted with at least one atom chosen from nitrogen and oxygen.

7. The compound according to claim 1, wherein the compound is chosen from N-[3-(3-aminopropylamino)propyl]benzene-1,4-diamine; N-(2-pyrrolidin-1-ylethyl)benzene-1,4-diamine; N-(3-pyrrolidin-1-ylpropyl)benzene-1,4-diamine; N-[3-(4-methylpiperazin-1-yl)propyl]benzene-1,4-diamine; 1-[3-(4-aminophenylamino)propyl]pyrrolidin-2-one; and N-{2-[2-(2-dimethyl aminoethoxy)ethoxy]ethyl}benzene-1,4-diamine.

8. The compound according to claim 1, wherein the compound is in the form of a salt.

9. The compound according to claim 8, wherein the compound is in the form of an acid addition salt chosen from hydrochlorides, hydrobromides, sulfates, citrates, succinates, tartrates, lactates, tosylates, benzenesulfonates, phosphates and acetates.

10. A method for preparing a compound, comprising performing a reduction reaction of the corresponding nitro compound, wherein the compound is an N-alkylamino secondary paraphenylenediamine of formula (I):

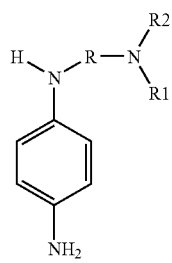

wherein:
- radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group,
- radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups,
- with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group,
- and with the proviso that the compound is not 4-[4-(piperidinyl)butylamino]aminobenzene, N-[3-(4-methylpiperazin-1-yl)propyl]benzene-1,4-diamine, or 4-[2-(piperidinyl)ethylamino]-aminobenzene
- and with the additional proviso that when R is a linear alkylene radical interrupted with a carbonyl functional group, and R1 and R2 are both hydrogen, then R must be methylene.

11. A process for dyeing keratin fibers, comprising applying to the keratin fibers at least one compound chosen from compounds of formula (I) and the addition salts thereof:

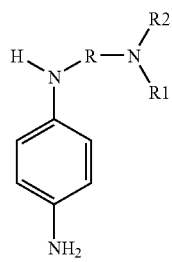

wherein:
- radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group,
- radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups,
- with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group,
- and with the additional proviso that when R is a linear alkylene radical interrupted with a carbonyl functional group, and R1 and R2 are both hydrogen, then R must be methylene.

12. A cosmetic composition for dyeing keratin fibers, comprising, in a medium suitable for dyeing, at least one compound chosen from compounds of formula (I) and the addition salts thereof:

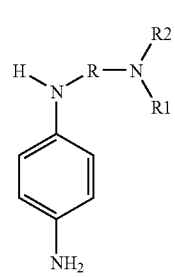

wherein:
- radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group,
- radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups,
- with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group and with the additional proviso that when R is a linear alkylene radical interrupted with a carbonyl functional group, and R1 and R2 are both hydrogen, then R must be methylene.

13. The composition according to claim 12, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins, and provitamins.

14. The composition according to claim 12, wherein the at least one compound of formula (I) is present in an amount ranging from 0.0001% to 20% by weight relative to the total weight of the composition.

15. The composition according to claim 14, wherein the at least one compound of formula (I) is present in an amount ranging from 0.005% to 6% by weight relative to the total weight of the composition.

16. The composition according to claim 12, wherein the medium suitable for dyeing comprises water or a mixture of water and at least one organic solvent.

17. The composition according to claim 13, wherein the at least one cosmetic adjuvant is present in an amount ranging from 0.01% to 20% by weight relative to the total weight of the composition.

18. The composition according to claim 12, further comprising at least one coupler chosen from meta-phenylenediamines, meta-aminophenols, meta-diphenols, naphthalene-based couplers and heterocyclic couplers, and the addition salts thereof.

19. The composition according to claim 18, wherein the at least one coupler is present in an amount ranging from 0.0001% to 20% by weight relative to the total weight of the composition.

20. The composition according to claim 12, further comprising at least one oxidation base other than the at least one compound of formula (I), chosen from para-phenylenediamines, bis(phenyl)alkylenediamines, para-aminophenols, ortho-aminophenols and heterocyclic bases, and the addition salts thereof.

21. The composition according to claim 20, wherein the at least one oxidation base other than the at least one compound of formula (I) is present in an amount ranging from 0.0001% to 20% by weight relative to the total weight of the composition.

22. The composition according to claim 12, further comprising at least one direct dye chosen from natural and cationic direct dyes.

23. The composition according to claim 12, wherein the composition is a ready-to-use composition further comprising at least one oxidizing agent chosen from hydrogen peroxide, urea peroxide, alkaline metal bromates, persalts, peracids and oxidase enzymes.

24. A process for dyeing keratin fibers, comprising applying to the keratin fibers a cosmetic composition for a time sufficient to develop a desired coloration, in the presence of at least one oxidizing agent, wherein the at least one oxidizing agent is applied before, simultaneously with or after the application of the composition, wherein the composition comprises, in a medium suitable for dyeing, at least one compound chosen from compounds of formula (I) and the addition salts thereof:

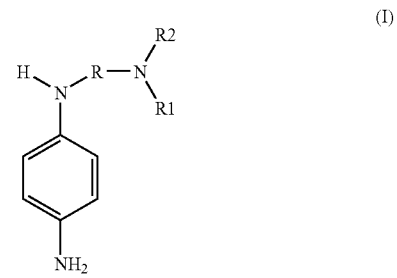

wherein:
radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group and with the additional proviso that when R is a linear alkylene radical interrupted with a carbonyl functional group, and R1 and R2 are both hydrogen. then R must be methylene.

25. A process for dyeing keratin fibers, comprising applying to the keratin fibers a ready-to-use composition for a time sufficient to develop a desired coloration, wherein the ready-to-use composition comprises, in a medium suitable for dyeing, at least one oxidizing agent, and
at least one compound chosen from compounds of formula (I) and the addition salts thereof:

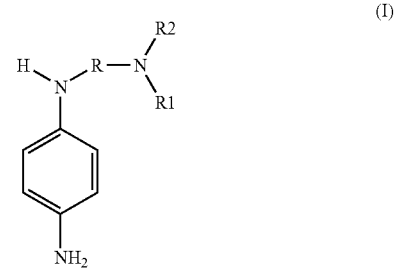

wherein:
radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group and with the additional proviso that when R is a linear alkylene radical interrupted with a carbonyl functional group, and R1 and R2 are both hydrogen, then R must be methylene.

26. A process for dyeing keratin fibers, comprising applying to the keratin fibers a composition comprising, in a medium suitable for dyeing, at least one compound chosen from compounds of formula (I) and the addition salts thereof:

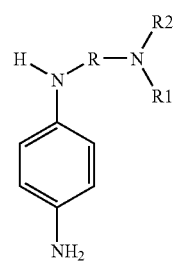

(I)

wherein:

radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group and with the additional proviso that when R is a linear alkylene radical interrupted with a carbonyl functional group, and R1 and R2 are both hydrogen, then R must be methylene.

27. A multi-compartment device, comprising a first compartment comprising a cosmetic composition for dyeing keratin fibers, comprising, in a medium suitable for dyeing, at least one compound chosen from compounds of formula (I) and the addition salts thereof:

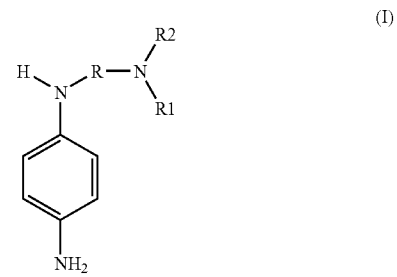

(I)

wherein:

radicals $R_1$ and $R_2$, which may be identical or different, are each chosen from a hydrogen atom, alkyl groups, monoalkylaminocarbonyl groups and dialkylaminocarbonyl groups, or the radicals $R_1$ and $R_2$ form, together with the nitrogen on which they are substituent, a saturated 5- or 6-membered ring optionally interrupted with at least one entity chosen from a nitrogen atom and a carbonyl functional group, and optionally substituted with at least one alkyl group, radical R is a linear or branched $C_1$-$C_{10}$ alkylene radical, optionally interrupted with at least one entity chosen from nitrogen and oxygen atoms and a carbonyl functional group, and optionally substituted with at least one group chosen from amino, monoalkylamino, dialkylamino, alkylcarbonyl, amido, monoalkylaminocarbonyl and dialkylaminocarbonyl groups, with the proviso that, when R is a linear or branched $C_1$-$C_{10}$ alkylene radical that is unsubstituted and not interrupted with at least one atom chosen from nitrogen and oxygen or with at least one carbonyl functional group, then the radicals $R_1$ and $R_2$ are not chosen from one of the following couples: two hydrogen atoms; two alkyl groups; and a hydrogen atom and an alkyl group, and with the additional Droviso that when R is a linear alkylene radical interruDted with a carbonyl functional group, and R1 and R2 are both hydrogen, then R must be methylene; and a second compartment comprising at least one oxidizing agent.

28. A composition as claimed in claim 12, wherein the compound of formula (I) is chosen from N-[3-(4-methylpiperazin-1-yl)propyl]benzene-1,4-diamine.

* * * * *

UNITED STATES PATENT AND TRADEMARK OFFICE
CERTIFICATE OF CORRECTION

PATENT NO.         : 7,338,536 B2                                           Page 1 of 1
APPLICATION NO. : 11/066456
DATED              : March 4, 2008
INVENTOR(S)        : Stéphane Sabelle et al.

It is certified that error appears in the above-identified patent and that said Letters Patent is hereby corrected as shown below:

Claim 24, col. 40, line 41, after "hydrogen" delete period and insert comma therefore.

Claim 27, col. 42, line 54, "Droviso" should read --proviso--.

Claim 27, col. 42, line 55, "interruDted" should read --interrupted--.

Signed and Sealed this

Eighth Day of July, 2008

JON W. DUDAS
*Director of the United States Patent and Trademark Office*